United States Patent [19]

Verrips et al.

[11] Patent Number: 4,966,842

[45] Date of Patent: * Oct. 30, 1990

[54] STRUCTURAL GENES ENCODING THE VARIOUS ALLELIC AND MATURATION FORMS OF PREPROTHAUMATIN RECOMBINANT CLONING VEHICLES, COMPRISING SAID STRUCTURAL GENES AND EXPRESSION THEREOF IN TRANSFORMED MICROBIAL HOST CELLS

[75] Inventors: Cornelis T. Verrips, Maassluis; Jan Maat, Monster; Luppo Edens, Maassluis; Adrianus M. Ledeboer, Rotterdam, all of Netherlands

[73] Assignee: Unilever Patent Holdings B.V., Rotterdam, Netherlands

[ * ] Notice: The portion of the term of this patent subsequent to Sep. 13, 2005 has been disclaimed.

[21] Appl. No.: 194,923

[22] Filed: May 17, 1988

Related U.S. Application Data

[63] Continuation of Ser. No. 732,818, May 10, 1985, Pat. No. 4,771,000, which is a continuation of Ser. No. 329,830, Dec. 11, 1981, abandoned.

[30] Foreign Application Priority Data

Dec. 12, 1980 [GB] United Kingdom ................ 8039854

[51] Int. Cl.$^5$ ...................... C12P 21/00; C12P 21/02; C12N 15/00; C12N 1/00; C12N 1/20; C07H 21/04
[52] U.S. Cl. .................................. 435/69.1; 536/27; 935/11; 435/70; 435/172.1; 435/172.3; 435/243; 435/252.3; 435/320; 435/71.1; 435/71.2
[58] Field of Search ............ 435/68, 70, 71, 91, 435/172.1, 172.3, 240.1, 240.2, 243, 253.2, 252.31–252.35; 530/370, 377, 379; 536/27

[56] References Cited

U.S. PATENT DOCUMENTS

| | | | |
|---|---|---|---|
| 4,237,224 | 12/1980 | Cohen et al. | 435/68 |
| 4,321,365 | 3/1982 | Wu et al. | 435/91 |
| 4,336,336 | 6/1982 | Silhavy et al. | 435/68 |

FOREIGN PATENT DOCUMENTS 1565190 4/1980 United Kingdom .

OTHER PUBLICATIONS

Roberts et al.; Proc. Natl. Acad. Sci. U.S.A. 76:760 (1979).
Henderson's Dictionary of Biological Terms, 1979, Holmes, Van Nostrand Reinhold Co., New York, p. 376.
Goeddel et al.; Nature 281:544 (1979).
Nature 284; 653 (1984).
Iyengar et al.: Chem. Abstr. 91:118895c (1979).
Helling et al.: in Genetic Engineering, 1978, Chakrabarty (ed.), CRC Press, pp. 1–30.
Messing: Recombinant DNA Technical Bulletin 2:43–48 (1979).
Stauffer et al.: Proc. Natl. Acad. Sci. U.S.A. 75:4833 (1978).
Iyengar et al.; Eur. J. Biochem. 96:194 (1979).
G. Blobel et al. (1975), J. Cell Biol. 67, 835–851.
D. Koshland et la. (1980), Cell 20, 749–760.
F. Lee et al., J. Mol. Biol. 121, 193–217 (1978).
K. Bertrand et al., Science 189, 22–26 (1975).

(List continued on next page.)

*Primary Examiner*—James Martinell
*Attorney, Agent, or Firm*—Cushman, Darby & Cushman

[57] ABSTRACT

The invention relates to structural genes consisting of DNA sequences encoding non-processed and partly processed thaumatin, to the various allelic forms of said non-processed thaumatin and to recombinant DNA's and plasmids comprising said structural genes coding for the various allelic forms of preprothaumatin, and naturally and/or artificially modified preprothaumatin in various stages of its natural processing, and to the use of said recombinant plasmids to transform microorganisms, particularly bacteria in which said genes are expressed.

6 Claims, 22 Drawing Sheets

OTHER PUBLICATIONS

P. M. G. F. Van Wezenbeek et al., Gene 11, 129–148 (1980).
K. S. Kirby (1965), Biochem. J. 96, 226–269.
U. Wiegers et al. (1972) FEBS Letters 23, 77–82.
H. Avir et al. (1972) Proc. Natl. Acad. Sci., U.S.A., 69, 1408–1412.
J. W. Davies et al. (1973), J. Virol. 12, 1434–1441.
G. N. Buell et al., J. Biol. Chem. (1978) 253, 2471–2482.
A. R. Davis et al., Gene 10, 205–218 (1980).
R. Roy Choudhury et al. (1976) Nucleic Acids Research 3, 863–877.
H. C. Birnbrim et al., Nucleic Acids Research 7, 1513–1523 (1974).
J. G. Williams et al., Cell 17, 903–913 (1979).
A. M. Maxam et al., Methods in Enzymology, L. Grossmann et al. editors: N.Y. Acad. Prss, 1980, vol. 65(1), pp. 499–560.
J. Maat et al., Nucleic Acids Research 5, 4537–4545 (1978).
D. Zimmern et al., Proc. Natl. Acad. Sci., U.S.A. 75, 4257–4261 (1978).
K. Backman et al., Cell 13, 65–71 (1978).
R. A. Hallewell et al., Gene 9, 27–47 (1980).
J. F. M. diRooy et al., Recl. Trav. Chim. Pays. Bas, 98, 537–548 (1979).
Edens et al., Gene. 18 (1982) 1–12 Elsevier Biomedical Press; Cloning of cDNA Encoding the Sweet-Tasting Plant Protein Thaumatin and Its Expression in Escherichia Coli.

Fig. 1

```
                                                    MET ALA ALA THR CYS PHE PHE LEU
AAAG CGC AGC CTC AAT TGG CAT CAT ACA TCA ATG GCC GCC ACC TGC TTC TTC CTC

62
    PHE PRO PHE LEU LEU LEU THR LEU SER ARG ALA ALA THR PHE GLU ILE VAL ASN ARG
    TTC CCC TTC CTC CTC CTC ACG CTC TCC CGC GCT GCC ACC TTC GAG ATC GTC AAC CGC

122
    CYS SER TYR THR VAL TRP ALA ALA SER LYS GLY ASP ALA ALA LEU ASP ALA GLY GLY
    TGC TCC TAC ACC GTG TGG GCC GCC TCC AAA GGC GAC GCC GCC CTG GAC GCC GGT GGC

182
    ARG GLN LEU ASN SER GLY GLU SER TRP ILE ASN VAL GLU PRO GLY THR LYS GLY GLY
    CGC CAG CTC AAC TCC GGA GAG TCC TGG ATC AAC GTA GAA CCC GGC ACC AAG GGT GGC

242
    LYS ILE TRP ALA ARG THR ASP CYS TYR PHE ASP ASP SER GLY ARG GLY ILE CYS ARG THR
    AAA ATC TGG GCC CGC ACC GAC TGC TAT TTC GAC GAC AGC GGC CGC GGC ATC TGC CGG ACC

302
    GLY ASP CYS GLY GLY LEU LEU GLN CYS LYS ARG PHE GLY ARG PRO PRO THR LEU ALA
    GGC GAC TGC GGC GGG CTC CTC CAG TGC AAG CGC TTC GGG CGC CCC ACC ACG CTG GCG

362
    GLU PHE SER LEU ASN GLN TYR GLY LYS ASP TYR ILE ASP ILE SER ASN ILE LYS GLY PHE
    GAG TTC TCG CTC AAC CAG TAC GGC AAG GAC TAC ATC GAC ATC TCC AAC ATC AAA GGG TTC

422
    ASN VAL PRO MET ASP PHE SER PRO THR THR ARG GLY CYS ARG GLY VAL ARG CYS ALA ALA
    AAC GTG CCC ATG GAC TTC AGC CCC ACC ACG CGG GGC TGC CGG GTG CGC TGC GCC GCC

482
    ASP ILE VAL GLY GLN CYS PRO ALA LYS LEU LYS ALA PRO GLY GLY GLY CYS ASN ASP ALA
    GAC ATC GTG GGG CAG TGC CCC GCG AAG CTG AAG GCG CCG GGC GGT TGC AAC GAT GCC
```

Continued

Continuation of Fig. 1

```
542
CYS THR VAL PHE GLN THR SER GLU TYR CYS CYS THR THR GLY LYS CYS GLY PRO THR GLU
TGC ACC GTG TTC CAG ACC AGC GAG TAC TGC TGC ACC ACG GGG AAG TGC GGG CCG ACG GAG

602
TYR SER ARG PHE PHE LYS ARG LEU CYS PRO ASP ALA PHE SER TYR VAL LEU ASP LYS PRO
TAC TCG CGC TTC TTC AAG AGG CTT TGC CCC GAC GCG TTC AGT TAT GTC CTG GAC AAG CCA

662
THR THR VAL THR CYS PRO GLY SER SER ASN TYR ARG VAL THR PHE CYS PRO THR ALA LEU
ACC ACC GTC ACC TGC CCC GGC AGC TCC AAC TAC AGG GTC ACT TTC TGC CCT ACT GCC CTT

722
GLU LEU GLU ASP GLU
GAA CTT GAA GAC GAG TAA GAG GAT GAA GAC GGA CAC TGA GGA TAC GCA ATA AAA GAA TAA

782
GAT GAT AAG CAA TTA TAT CAA TAA AAA GGG TAC GTG GTT TGG CCA TTG GCT AAT TAA ACT TGT AAA ATA

842
TGG GAG CAA AAG TGT TAT AAA ATA TGT GTC TGG CCA TTG GCT AAT TAA ACT TGT AAA ATA

902
TAA ATA AAA GTT CTC CGT TTT GAG GTG TGC AAA AAA AAA AAA AAA AAA AAA AAA AAA AAA
```

Fig. 2

```
32
MET ALA ALA THR THR CYS PHE PHE PHE LEU PHE PRO PHE LEU LEU LEU LEU THR LEU SER
ATG GCC GCC ACC ACT TGC TTC TTC TTC CTC TTC CCC TTC CTC CTC CTC CTC ACG CTC TCC

92
ARG ALA ALA THR PHE GLU ILE VAL ASN ARG CYS SER TYR THR VAL TRP ALA ALA ALA SER
CGC GCT GCC ACC TTC GAG ATC GTC AAC CGC TGC TCC TAC ACC GTG TGG GCG GCC GCC TCC

152
LYS GLY ASP ALA ALA LEU ASP ALA GLY GLY ARG GLN LEU ASN SER GLY GLU SER TRP THR
AAA GGC GAC GCC GCC CTG GAC GCC GGC GGC CGC CAG CTC AAC TCG GGA GAG TCC TGG ACC

212
ILE ASN VAL GLU PRO GLY THR LYS GLY GLY LYS ILE TRP ALA ARG THR ASP CYS TYR PHE
ATC AAC GTA GAA CCC GGC ACC AAG GGT GGC AAA ATC TGG GCC CGC ACC GAC TGC TAT TTC

272
ASP ASP SER GLY ARG GLY ILE CYS ARG THR GLY ASP CYS GLY GLY LEU LEU GLN CYS LYS
GAC GAC AGC GGC CGC GGC ATC TGC CGG ACC GGC GAC TGC GGC GGC CTC CTC CAG TGC AAG

332
ARG PHE GLY ARG PRO PRO THR THR LEU ALA GLU PHE SER LEU ASN GLN TYR GLY LYS ASP
CGC TTC GGC CGG CCG CCC ACC ACG CTG GCG GAG TTC TCG CTC AAC CAG TAC GGC AAG GAC

392
TYR ILE ASP ILE SER ASN ILE LYS GLY PHE ASN VAL PRO MET ASP PHE SER PRO THR THR
TAC ATC GAC ATC TCC AAC ATC AAA GGC TTC AAC GTG CCC ATG GAC TTC AGC CCC ACC ACG

452
ARG GLY CYS ARG GLY VAL ARG CYS ALA ALA ASP ILE VAL GLY GLN CYS PRO ALA LYS LEU
CGC GGC TGC CGC GGG GTG CGG TGC GCC GCC GAC ATC GTG GGG CAG TGC CCG GCG AAG CTC

512
LYS ALA PRO GLY GLY GLY CYS ASN ASP ALA CYS THR VAL PHE GLN THR SER GLU TYR CYS
AAG GCG CCG GGC GGT GGT TGC AAC GAT GCG TGC ACC GTG TTC CAG ACG AGC GAG TAC TGC

572
CYS THR THR GLY LYS CYS GLY PRO THR GLU TYR SER ARG PHE PHE LYS ARG LEU CYS PRO
TGC ACC ACC GGG AAG TGC GGG CCG ACG GAG TAC TCG CGC TTC TTC AAG AGG CTT TGC CCC

632
ASP ALA PHE SER TYR VAL LEU ASP LYS PRO THR THR VAL THR CYS PRO GLY SER SER ASN
GAC GCG TTC AGT TAT GTC CTC GAC AAG CCA ACC ACC GTC ACC TGC CCC GGC AGC TCC AAC

692
TYR ARG VAL THR PHE CYS PRO THR ALA LEU GLU LEU GLU ASP GLU
TAC AGG GTC ACT TTC TGC CCT ACT GCC CTT GAA CTT GAA GAC GAG
```

Fig. 3

```
98
ALA THR PHE GLU ILE VAL ASN ARG CYS SER TYR THR VAL TRP ALA ALA ALA SER LYS GLY
GCC ACC TTC GAG ATC GTC AAC CGC TGC TCC TAC ACC GTG TGG GCC GCC GCC TCC AAA GGC

158
ASP ALA ALA LEU ASP ALA GLY GLY ARG GLN LEU ASN SER GLY GLU SER TRP THR ILE ASN
GAC GCC GCC CTG GAC GCC GGC GGC CGC CAG CTC AAC TCG GGA GAG TCC TGG ACC ATC AAC

218
VAL GLU PRO GLY THR LYS GLY GLY LYS ILE TRP ALA ARG THR ASP CYS TYR PHE ASP ASP
GTA GAA CCC GGC ACC AAG GGT GGC AAA ATC TGC GCC CGC ACC GAC TGC TAT TTC GAC GAC

278
SER GLY ARG GLY ILE CYS ARG THR GLY ASP CYS GLY GLY LEU LEU GLN CYS LYS ARG PHE
AGC GGC CGC GGC ATC TGC CGG ACC GGC GAC TGC GGC GGC CTC CTC CAG TGC AAG CGC TTC

338
GLY ARG PRO PRO THR THR LEU ALA GLU PHE SER LEU ASN GLN TYR GLY LYS ASP TYR ILE
GGC CGG CCG CCC ACC ACG CTG GCG GAG TTC TCG CTC AAC CAG TAC GGC AAG GAC TAC ATC

398
ASP ILE SER ASN ILE LYS GLY PHE ASN VAL PRO MET ASP PHE SER PRO THR THR ARG GLY
GAC ATC TCC AAC ATC AAA GGC TTC AAC GTG CCG ATG GAC TTC AGC CCG ACC ACG CGC GGC

458
CYS ARG GLY VAL ARG CYS ALA ALA ASP ILE VAL GLY GLN CYS PRO ALA LYS LEU LYS ALA
TGC CGC GGG GTG CGG TGC GCC GCC GAC ATC GTG GGG CAG TGC CCG GCG AAG CTG AAG GCG

518
PRO GLY GLY GLY CYS ASN ASP ALA CYS THR VAL PHE GLN THR SER GLU TYR CYS CYS THR
CCG GGC GGT GGT TGC AAC GAT GCG TGC ACC GTG TTC CAG ACG AGC GAG TAC TGC TGC ACC

578
THR GLY LYS CYS GLY PRO THR GLU TYR SER ARG PHE PHE LYS ARG LEU CYS PRO ASP ALA
ACG GGG AAG TGC GGG CCG ACG GAG TAC TCG CGC TTC TTC AAG AGG CTT TGC CCG GAC GCG

638
PHE SER TYR VAL LEU ASP LYS PRO THR THR VAL THR CYS PRO GLY SER SER ASN TYR ARG
TTC AGT TAT GTC CTG GAC AAG CCA ACC ACC GTC ACC TGC CCC GGC AGC TCC AAC TAC AGG

698
VAL THR PHE CYS PRO THR ALA LEU GLU LEU GLU ASP GLU
GTC ACT TTC TGC CCT ACT GCC CTT GAA CTT GAA GAC GAG
```

Fig. 4

```
32
MET ALA ALA THR THR CYS PHE PHE PHE LEU PHE PRO PHE LEU LEU LEU LEU THR LEU SER
ATG GCC GCC ACC ACT TGC TTC TTC TTC CTC TTC CCC TTC CTC CTC CTC CTC ACG CTC TCC

92
ARG ALA ALA THR PHE GLU ILE VAL ASN ARG CYS SER TYR THR VAL TRP ALA ALA ALA SER
CGC GCT GCC ACC TTC GAG ATC GTC AAC CGC TGC TCC TAC ACC GTG TGG GCG GCC GCC TCC

152
LYS GLY ASP ALA ALA LEU ASP ALA GLY GLY ARG GLN LEU ASN SER GLY GLU SER TRP THR
AAA GGC GAC GCC GCC CTG GAC GCC GGC GGC CGC CAG CTC AAC TCC GGA GAG TCC TGG ACC

212
ILE ASN VAL GLU PRO GLY THR LYS GLY GLY LYS ILE TRP ALA ARG THR ASP CYS TYR PHE
ATC AAC GTA GAA CCC GGC ACC AAG GGT GGC AAA ATC TGG GCC CGC ACC GAC TGC TAT TTC

272
ASP ASP SER GLY ARG GLY ILE CYS ARG THR GLY ASP CYS GLY GLY LEU LEU GLN CYS LYS
GAC GAC AGC GGC CGC GGC ATC TGC CGG ACC GGC GAC TGC GGC GGC CTC CTC CAG TGC AAG

332
ARG PHE GLY ARG PRO PRO THR THR LEU ALA GLU PHE SER LEU ASN GLN TYR GLY LYS ASP
CGC TTC GGC CGG CCG CCC ACC ACG CTG GCG GAG TTC TCG CTC AAC CAG TAC GGC AAG GAC

392
TYR ILE ASP ILE SER ASN ILE LYS GLY PHE ASN VAL PRO MET ASP PHE SER PRO THR THR
TAC ATC GAC ATC TCC AAC ATC AAA GGC TTC AAC GTG CCG ATG GAC TTC AGC CCG ACC ACG

452
ARG GLY CYS ARG GLY VAL ARG CYS ALA ALA ASP ILE VAL GLY GLN CYS PRO ALA LYS LEU
CGC GGC TGC CGC GGG GTG CGG TGC GCC GCC GAC ATC GTG GGG CAG TGC CCC GCG AAG CTG

512
LYS ALA PRO GLY GLY GLY CYS ASN ASP ALA CYS THR VAL PHE GLN THR SER GLU TYR CYS
AAG GCG CCG GGG GGT GGT TGC AAC GAT GCC TGC ACC GTG TTC CAG ACG AGC GAG TAC TGC

572
CYS THR THR GLY LYS CYS GLY PRO THR GLU TYR SER ARG PHE PHE LYS ARG LEU CYS PRO
TGC ACC ACG GGG AAG TGC GGG CCG ACG GAG TAC TCG CGC TTC TTC AAG AGG CTT TGC CCG

632
ASP ALA PHE SER TYR VAL LEU ASP LYS PRO THR THR VAL THR CYS PRO GLY SER SER ASN
GAC GCG TTC AGT TAT GTC CTG GAC AAG CCA ACC ACC GTC ACC TGC CCC GGC AGC TCC AAC

692
TYR ARG VAL THR PHE CYS PRO THR ALA
TAC AGG GTC ACT TTC TGC CCT ACT GCC
```

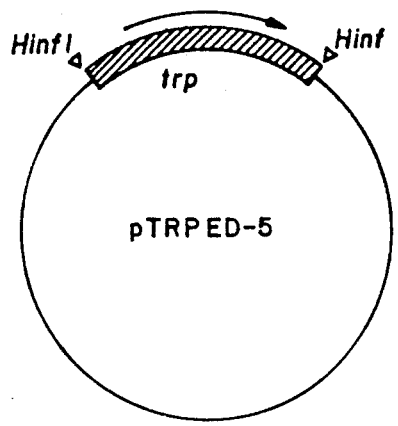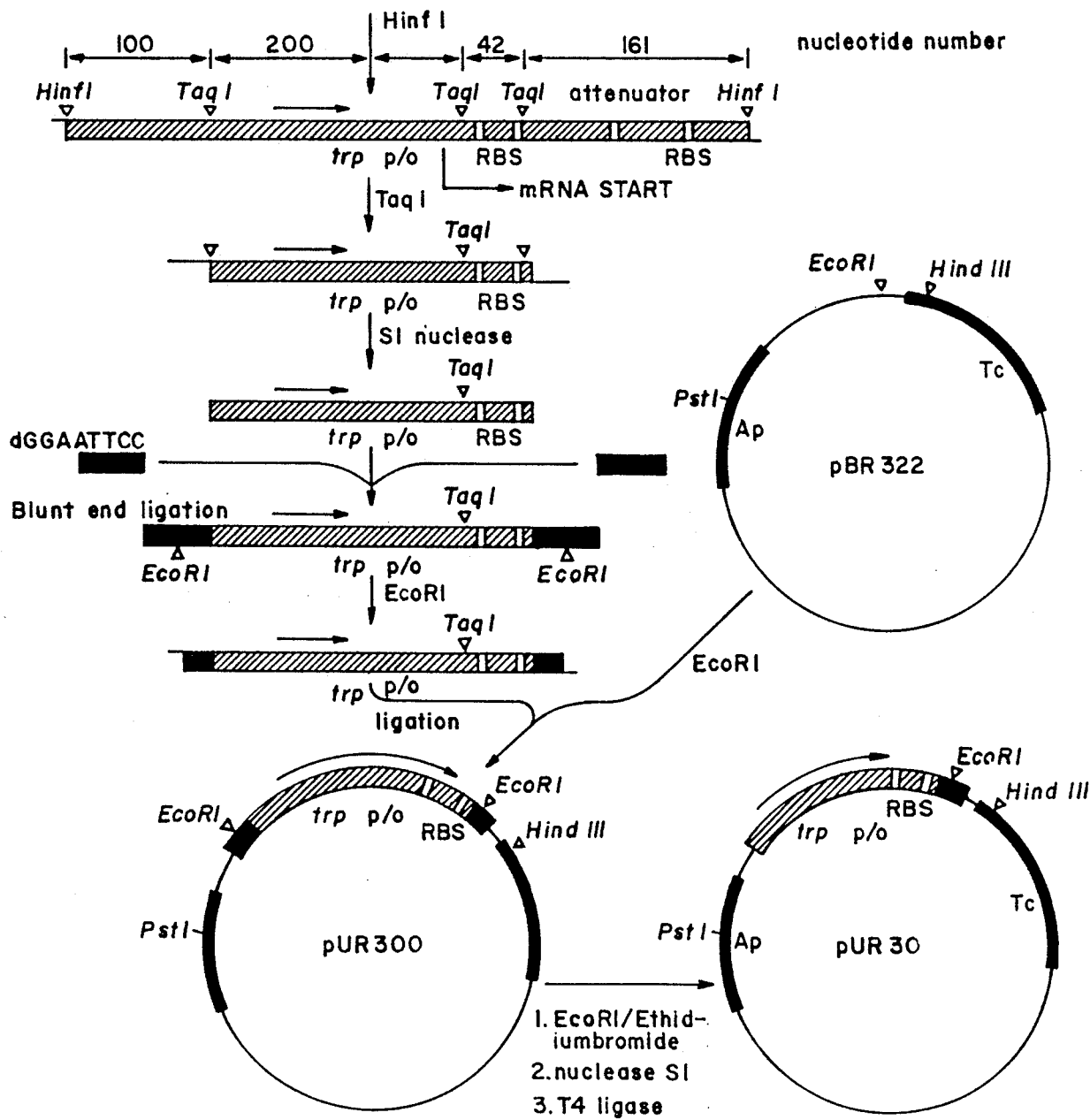
Fig. 8

Fig. 10.
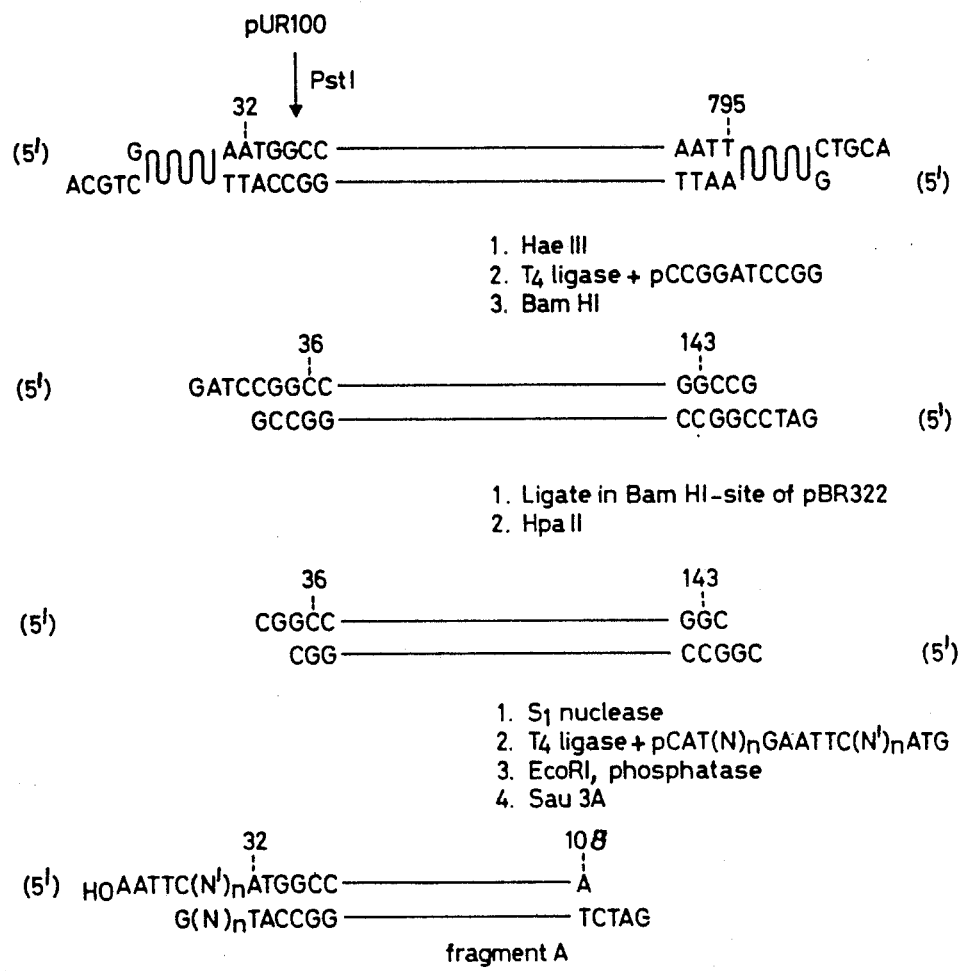
 = G/C-stretch

STRUCTURAL GENES ENCODING THE VARIOUS ALLELIC AND MATURATION FORMS OF PREPROTHAUMATIN RECOMBINANT CLONING VEHICLES, COMPRISING SAID STRUCTURAL GENES AND EXPRESSION THEREOF IN TRANSFORMED MICROBIAL HOST CELLS

This is a continuation of application Ser. No. 732,818, filed May 10, 1985 now U.S. Pat. No. 4,711,000, which is a continuation of Ser. No. 329,830 filed Dec. 11, 1981, abandoned.

The present invention relates to structural genes consisting encoding non-processed and partly processed thaumatin, to the various allelic forms of said non-processed thaumatin and to recombinant DNA's and plasmids comprising said structural genes coding for the various allelic forms of preprothaumatin, and naturally and/or artificially modified preprothaumatin in various stages or its natural processing, and to the use of said recombinant plasmids to transform microorganisms, particularly bacteria in which said genes are expressed.

Thaumatin is a protein originating from the arils of the fruit of *Thaumatococcus daniellii*. Thaumatin is, on a weight basis, 1600 times sweeter than sucrose and on a molecular basis $10^5$ times sweeter than sucrose. In Western society overconsumption of sugar causes a number of health problems. Therefore, many attempts have been made to substitute low caloric sweeteners for sugar. However, several of these have recently been prohibited in view of possible side-effects. There is thus a need for a natural low caloric sweetener and for an economical process of producing such a sweetener. Recent advances in molecular biology have enabled the introduction of genes coding for specific eukaryotic proteins into microbial host cells and expressing said genes in the transformed host cells, thereby producing the desired protein.

Many genes of eukaryotic origin which in their natural state encode proteins in their unprocessed forms, can not be applied directly in recombinant DNA molecules because natural genes contain DNA sequences called introns, which are not contained in the messenger RNA (mRNA).The information located on these introns is removed in eukaryotic cells before the translation process of the mRNA. As far as Applicants are aware, bacteria are unable to excise such introns at the RNA level and therefore it is necessary to remove the genetic information located on these introns at DNA level before the natural gene of eukaryotes can be used in prokaryotic host cells.

In microbial host cells, that have the capability of excising introns at mRNA level, the natural genes can in principle be applied, provided that they are brought under control of regulons that are effective in said microbial host cells.

For economic reasons it is important that proteins encoded by the recombinant DNA gene are produced under optimal conditions. The main routes to achieve this are:

(1) integration of the structural gene down-stream of an effective regulon, in such a way that under selected growth conditions, the amount of protein produced per cell (by an optimal number of cells) is as high as possible.

For that purpose regulons like the double lac UV5 and the trp regulon of *E. coli* and the regulon of the gene VIII product of the bacteriophages M13, fd and fl are, amongst others, adequate in their natural state or in their processed form(s).

(2) excretion of said protein by microbial host cells into their periplasmic space and/or into the culturing medium, thus preventing said protein from intracellular degradation or preventing the disturbance of the normal cellular processes due to too high an intracellular level of said protein. It is now generally accepted that in many prokaryotic and eukaryotic cells a special $NH_2$-terminal amino acid sequence of the unprocessed form of the proteins is involved in the protein excretion process. G. Blobel and B. Dobberstein (1975), J. Cell Biol. 67, 835–851.

Recently it was proved that also the COOH-terminal amino acid sequence of the protein can also play a role in this process. D. Koshland and D. Botstein (1980), Cell 20, 749–760.

Therefore it would be of high economic importance if proteins encoded by recombinant DNA molecules had at their $NH_2$- and/or COOH- terminus amino acid sequences that promote the excretion of said proteins by microbial cells.

In the present invention use is made of recombinant DNA and other molecular biological techniques to construct recombinant DNA molecules that fulfil the above-described requirements.

The present invention is also related to the change of the genetic information of structural genes using site-directed mutagenesis.

For a better understanding of the invention the most important terms used in the description will be defined:
A regulon is a DNA sequence consisting of a promotor and operator region.
Structural genes are DNA sequences which encode through a template (mRNA) a sequence of amino acids characteristic of a specific polypeptide.
A promoter is a DNA sequence within the regulon to which RNA polymerase binds for the initiation of the transcription.
An operator is a DNA sequence within the regulon to which a repressor protein may bind, thus preventing RNA polymerase from binding to the adjacent promoter
An inducer is a substance which deactivates a repressor protein, freeing the operator and permitting RNA polymerase to bind to the promoter and start transcription.
By preprothaumatin is meant one of the allelic forms of the unprocessed protein (FIG. 4).
Cloning vehicle. A non-chromosomal double-stranded DNA, plasmid or phage, comprising a DNA sequence (intact replicon) that allows self-replication after transformation into suitable host cells.
Phage or bacteriophage. Bacterial virus which can replicate in a suitable bacterial host cell.
Reading frame. The grouping of triplets of nucleotides (codons) into such a frame that at mRNA level a proper translation of the codons into the polypeptide takes place.
Transcription. The process of producing RNA from a gene.
Translation. The process of producing a polypeptide from mRNA.
Expression. The process undergone by a structural gene to produce a polypeptide. It is a combination of many processes, including at least transcription and translation.

By preprothaumatin gene is meant the double-stranded DNA sequence having exactly the same information (sequence of codons) as that part of the messenger RNA coding for unprocessed preprothaumatin.

By signal peptide is meant that part of the preproprotein which has a high affinity to biomembranes and/or which is involved in the transport of the preproprotein through biomembranes. These transport processes are often accompanied by processing of the preproprotein into one of the mature forms of the protein.

Double-stranded nucleotide sequences will be shown as only one strand, for convenience.

BRIEF DESCRIPTION OF THE DRAWINGS

FIGS. 1–4 show amino acid and nucleotide sequences of various forms of preprothaumatin, prothaumatin, and prethaumatin.

FIGS. 7–9 illustrate the construction of plasmids pUR201, pUR301, and pUR 401 respectively.

FIG. 10 shows the construction of the preprothaumatin gene without G/C-tails.

According to the invention a recombinant plasmid is provided comprising:

(i) structural genes coding for the various allelic forms of preprothaumatin or mutated forms of these structural genes (FIGS. 2, 3, 4, 5, 6).

Figure 7:
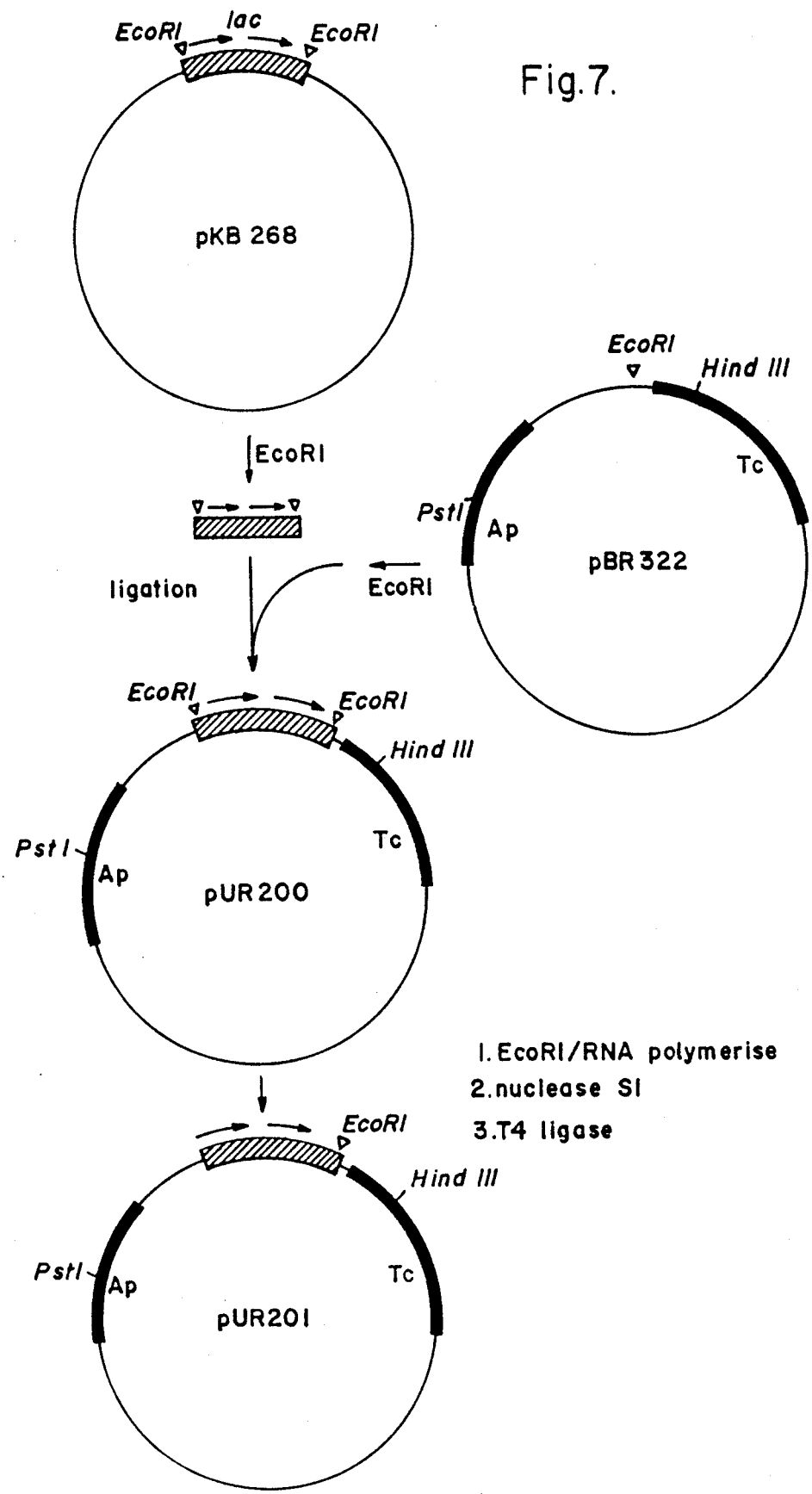

(ii) specific DNA sequences which regulate the expression of said structural genes. These specific DNA sequences consist of either an inducible or a constitutive regulon. A preferred inducible regulon consists of a double lac UV5 system as described by Goeddel et al., Nature 281, 544–548 (1979), plasmid pUR 201 (FIG. 7).

Another preferred inducible regulon is a constituent of the tryptophan system described by F. Lee et al., J. Mol. Biol. 121, 193–217 (1978) and K. Bertrand et al., Science 189, 22–26 (1975).

Applicants have modified this tryptophan system to obtain a more adequate system according to FIG. 8. In this modified system the attenuator region and the information for the 14-residue peptide in the leader transcript has been eliminated, while maintaining the ribosome binding site of the latter protein.

Figure 9:
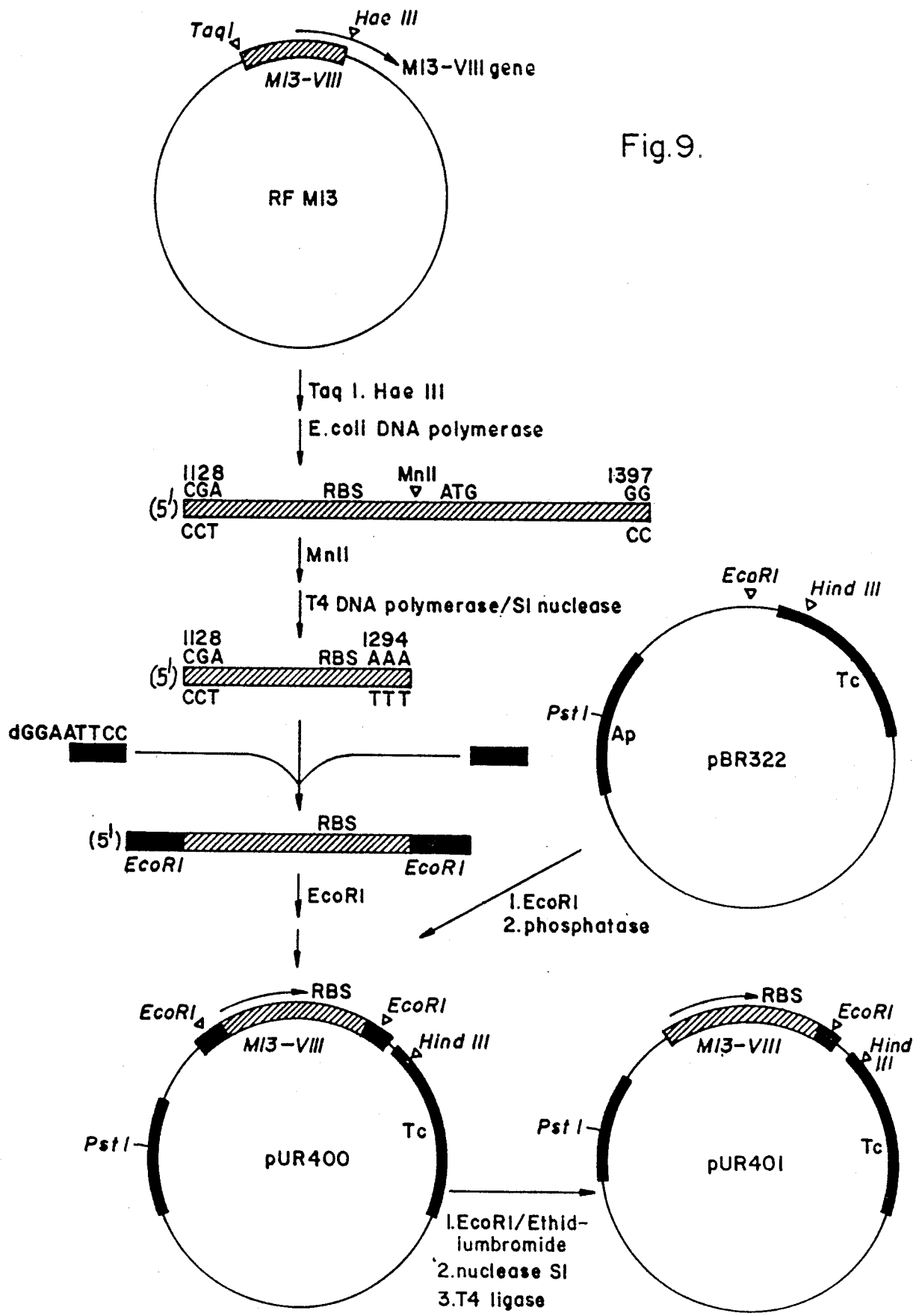

Also preferred are recombinant plasmids according to the invention which comprise DNA sequences consisting of a modified promoter/ribosome-binding site (FIG. 9) of gene VIII of bacteriophage M13, fd or fl, P. M. G. F. van Wezenbeek et al., Gene 11, 29–148 (1980), which, as far as Applicants are aware, were never used before for the expression of eukaryotic genes.

In the recombinant plasmid according to the invention the regulon may be either directly linked to the structural gene or indirectly through a novel start codon and EcoRI containing DNA linker comprising the nucleotide sequence (5')pCAT(N)$_n$GAATTC(N'-)$_n$ATG$_{OH}$(3') wherein $n=0, 1, 2$ or $3$, and N and N' are any of the nucleotide A, T, G or C, with the proviso that in the double-stranded structure N and N' are such that a rotational symmetrical structure is present. By a rotational symmetrical structure is meant that were N is e.g. represented by A, N' should be represented by the complementary base T.

Figure 5:
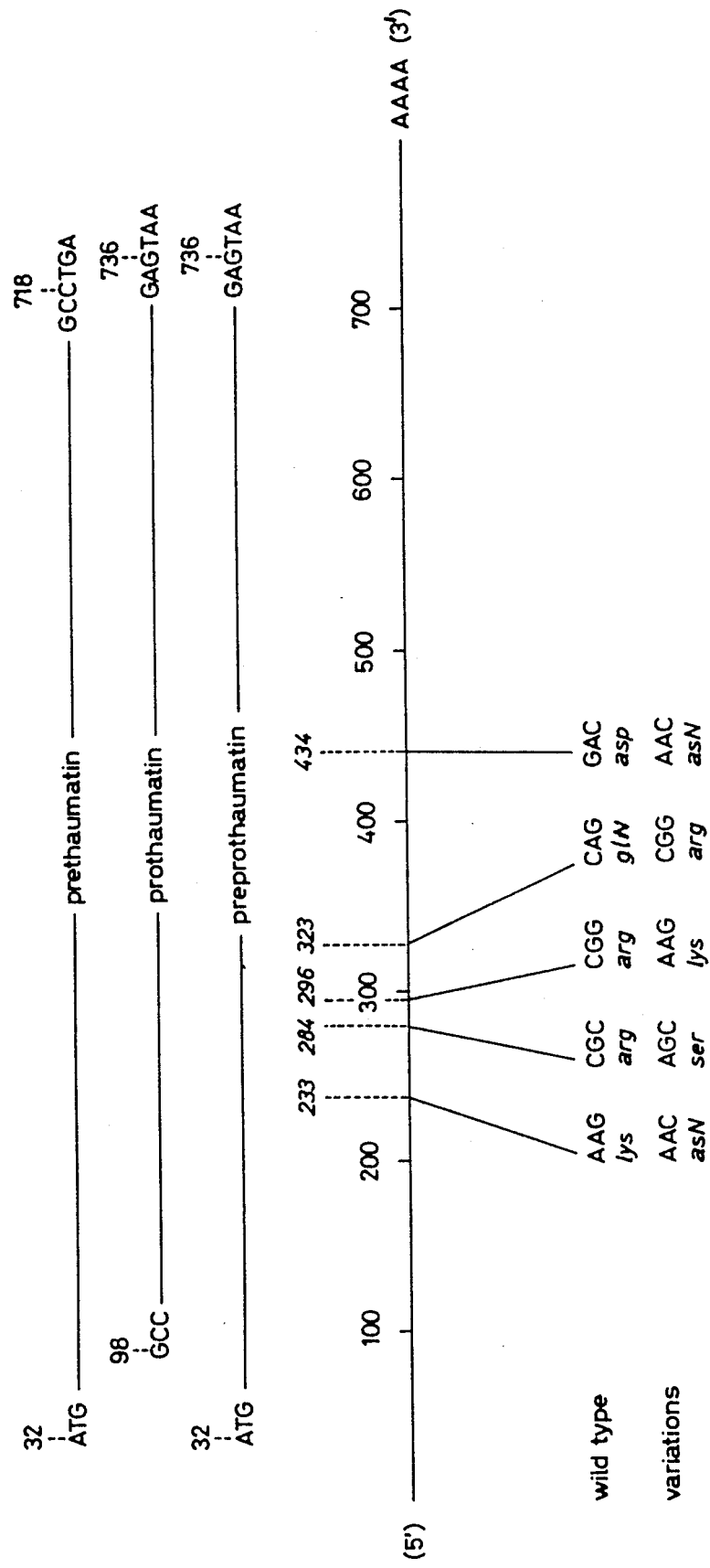
FIG. 5 illustrates allelic variations in the prepothaumatin gene.
Figure 6:
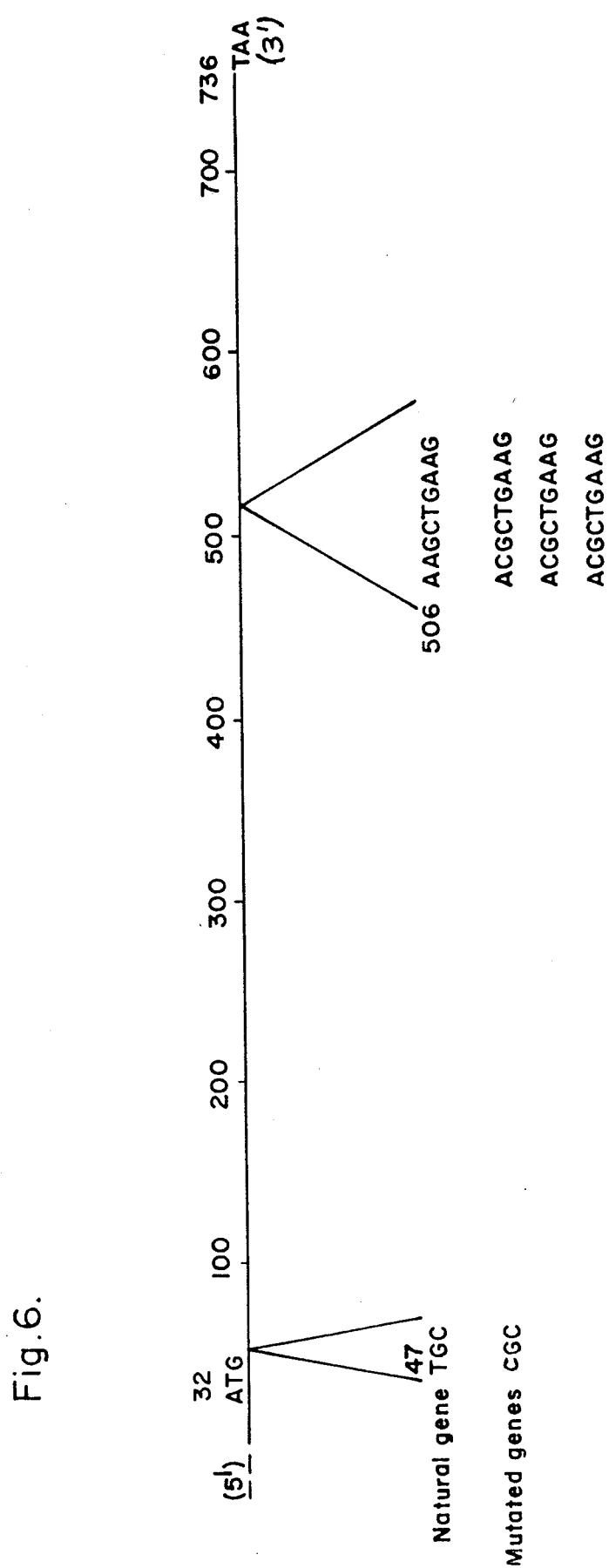
FIG. 6 shows some mutations introduced in the various allelic genes according preprothaumatin.

In some instances it turned out that the yield of expression improved when the sequence AATT between the regulon and the structural gene had been eliminated. The microbial cloning vehicles containing the natural or mutated structural genes encoding the various allelic forms of the preprothaumatin according to the invention are obtained and the various preprothaumatins are produced by performing a number of steps, the most essential of which are:

(1) isolation and purification of the messenger RNA (mRNA) of thaumatin;

(2) conversion of this mRNA into double-stranded DNA (ds DNA);

(3) construction of ds DNA having a poly-dC tail;

(4) incorporation of the ds DNA-poly-dC molecules in Pst I-cleaved and poly-dG-tailed plasmid pBR 322 DNA;

(5) transformation and clone selection;

(6) determination of the nature of the inserts by RNA/DNA hybridization and in vitro translation;

(7) double-checking the nature of the inserts by DNA- and RNA-sequence analysis;

(8a) producing DNA encoding the unprocessed preprothaumatin (FIGS. 1, 2 and 5);

(8b) producing DNA encoding prothaumatin (FIG. 3);

(8c) producing DNA encoding prothaumatin (FIG. 4);

(8d) producing DNA encoding the unprocessed preprothaumatin, except that special mutations have been introduced into the nucleotide sequence 32–97, particularly into the nucleotides 32–49 (FIG. 1,6);

(8e) producing DNA as described under (8a–8i d), except that special mutations have been introduced into the nucleotide sequence 32–736, particularly into the nucleotide sequence 332–718 (FIG. 1,6);

(9) construction of plasmids comprising specific transcription regulating DNA-sequences, and chemical synthesis of DNA-linkers and -primers;

(10) construction of plasmids comprising a constitutive or inducible regulon and the ligated preprothaumatin genes as described under (8a–8e) and transformation of E. coli with said plasmids.

(11) culturing of E. coli cells containing said recombinant plasmids and detection and isolation of the preprothaumatins or their naturally processed forms.

The following detailed description will illustrate the invention.

1. Isolation and purification of mRNA (thaumatin)

Isolated arils of Thaumatococcus daniellii were ground under liquid nitrogen. After protein extraction with phenol, a selective precipitation of the RNAs with LiCl was performed following the procedure described by K. S. Kirby (1965), Biochem. J. 96, 226–269, U. Wiegers and H. Hilz (1972) FEBS Letters 23, 77–82. Poly-A containing messenger RNA was recovered by several passages over oligo-dT-cellulose columns and from this messenger mixture the thaumatin-encoding mRNA, was isolated by polyacrylamide electrophoresis. This was checked by translation of the mRNA in the wheat germ system as described by H. Aviv and P. Leder (1972) Proc. Natl. Acad. Sci., U.S.A., 69, 1408-1412, J. W. Davies and P. Kaesburg (1973), J. Virol. 12, 1434-1441.

2. Conversion of mRNA thaumatin into double-stranded DNA

The purified thaumatin mRNA was copied with AMV reverse transcriptase to yield a single-stranded DNA molecule, according to the procedure described by G. N. Buell et al., J. Biol. Chem. (1978) 253, 2471-2482. This DNA was subsequently converted into a double-stranded molecule by using E. coli DNA-polymerase, according to the procedure described by A. R. Davis et al., Gene 10, 205-218 (1980) The loop structure of the double-stranded DNA copy was removed by nuclease-S1-digestion.

3. Construction of double-stranded DNA with poly-dC tails

DNA-molecules of the desired length were obtained by polyacrylamide gel-electrophoresis, extracted from the gel an tailed with poly-dC by terminal transferase according to the procedure described by R. Roychoudhury et al., (1976) Nucleic Acids Research 3, 863-877.

4. Integration of the ds DNA-poly-dC molecules in the plasmid pBR 322

Plasmid pBR 322 was treated with the restriction endonuclease Pst I, that cleaves the plasmid at a recognition site that lies in the gene encoding the β-lactamase protein.

Subsequently pBR 322 was supplied with poly-dG tails by terminal transferase. The poly-dC DNA molecules were annealed to the poly-dG tailed plasmid pBR 322.

5. Transformation and clone selection

The plasmids thus obtained were transferred into CaCl$_2$-treated E. coli cells. After transformation cells containing hybrid plasmid DNA molecules were selected on their resistance to tetracycline. Positive colonies were screened for plasmids with large inserts by a combination of a rapid plasmid extraction procedure as outlined by H. C. Birnboim and J. Doly, Nucleic Acids Research 7, 1513-1523 (1979) and Pst I-digestion of the isolated DNA.

6. Determination of the nature of the inserts (I). Hybridization/in vitro translation From the selected clones 10 μg plasmid DNA were isolated, which subsequently were bound to diazotated (DBM) paper discs. The immobilized plasmid DNA molecules were then used in a hybridization/in vitro translation procedure as outlined by J. G. Williams et al., Cell 17, 903-913 (1979) in order to determine the nature of the DNA insert.

7. Determination of the nature inserts (II) by DNA- and RNA sequence analysis

The nucleotide sequence analysis of the thaumatin inserts was performed by the chemical degradation procedure as outlined by A. M. Maxam and W. Gilbert in Methods in Enzymology, L. Grossmann and K. Moldave editors, New York, Acad. Press, 1980, Vol. 65(1), pages 499-560, and by the dideoxy/nick translation procedure as outlined by J. Maat and A. J. H. Smith, Nucleic Acids Research 5, 4537-4545 (1978). Further information on the nucleotide sequence of the thaumatin mRNA was derived indirectly by primed synthesis by AMV-reverse transcriptase on the thaumatin mRNA template in the presence of chain terminating inhibitors, as outlined by D. Zimmern and P. Kaesberg, Proc. Natl. Acad. Sci., U.S.A. 75, 4257-4261 (1978). This screening yielded inter alia plasmid pUR 100 containing an almost complete copy of thaumatin mRNA.

8. Production of DNA encoding various maturation forms of preprothaumatin

8a. Production of DNA encoding for the unprocessed preprothaumatin

Plasmid pUR 100 was treated with the restriction endonuclease Pst I and the DNA sequence containing at least the nucleotides 31-793 (FIG. 1) was subsequently treated with restriction endonuclease Hae III generating inter alia a DNA fragment running from position 36-143. This fragment was blunt-end ligated with the chemically synthesized linker (5')pCCGGATCC-GG$_{OH}$(3'), then treated with the restriction endonuclease Bam HI, subsequently ligated in the restriction endonuclease Bam HI site of pBR 322 and cloned in E. coli. Plasmid DNA containing the cloned fragment was treated with Hpa II and S1 nuclease, resulting in the nucleotide sequence

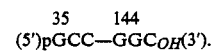

(5')pGCC—GGC$_{OH}$(3').

This sequence was blunt end ligated to the chemically synthesized linker (5')pCA GAATTC(N)$_n$ATG$_{OH}$(3'), treated with restriction endonuclease EcoRI, subsequently integrated in the EcoRI site of pBR 322 and cloned in E. coli.

The plasmids with the preprothaumatin insert were treated with EcoRI and restriction endonuclease Sau 3A, resulting in fragment A of FIG. 10.

Figure 11:
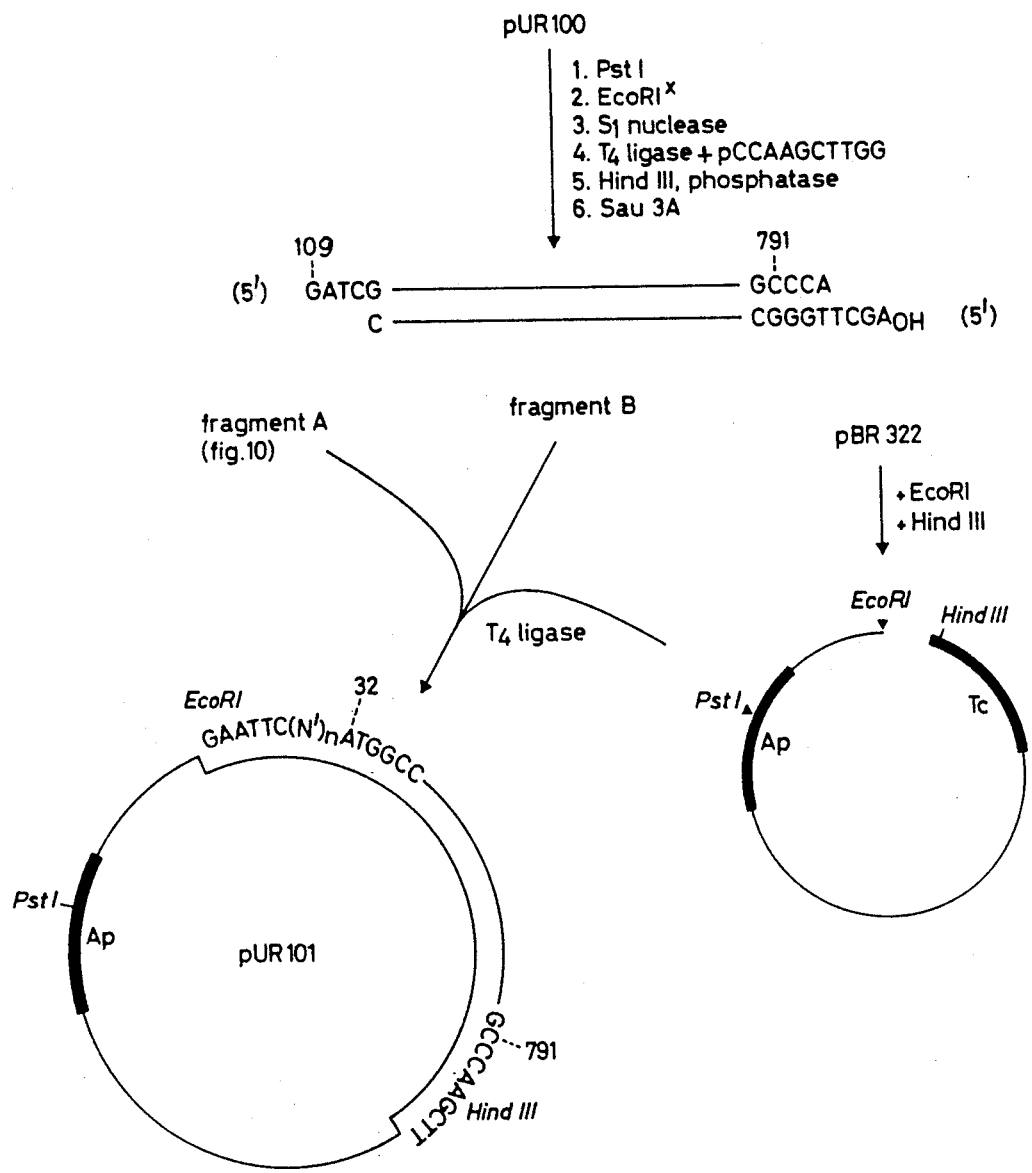
FIGS. 11–14 illustrate the construction of pUR101, M13-101-A, and M13-101-B, pUR102, and pUR103 respectively.

Plasmid pUR 100 was treated with restriction endonuclease Pst I and with EcoRI in the presence of Mn++ (1 mmol/l). Under this condition EcoRI recognize the sequence AATT. After S1 nuclease treatment this DNA fragment was blunt-end ligated with the chemically synthesized linker (5')pCCAAGCTT-GG$_{OH}$(3') and subsequently treated with restriction endonucleases Hind III and Sau 3A resulting in fragment B (with Sau 3A site at nucleotide position 109 and a Hind III site after position 791). The fragments A and B were ligated and subsequently integrated into the EcoRI and Hind III treated pBR 322, resulting in plasmid pUR 101 (FIG. 11).

A single-stranded DNA template was obtained by cloning the EcoRI-Hind III fragment of pUR 101, after repair synthesis with Klenow-DNA polymerase and addition of EcoRI-linker (5')pGGAATTCC$_{OH}$(3') in the EcoRI site of RF M13-mp2.

Figure 12:
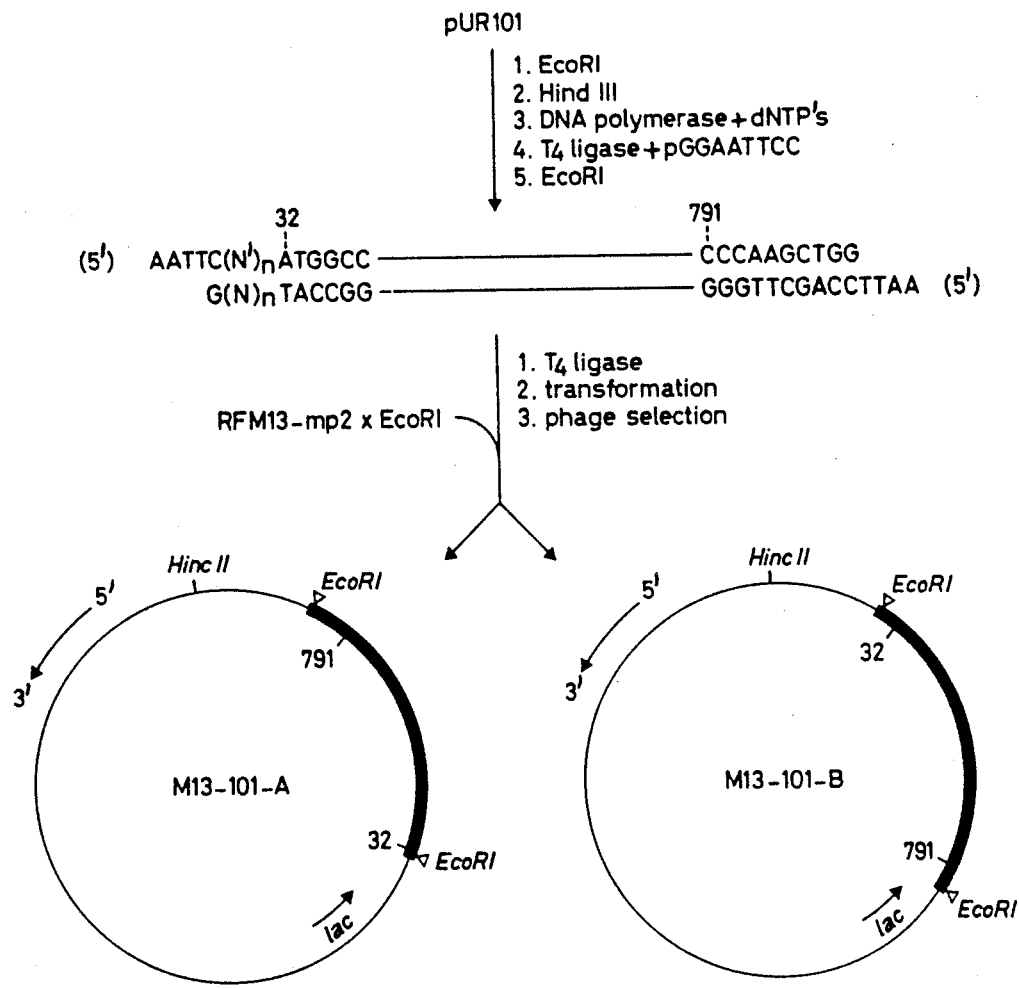

Clone M13-101-A has the preprothaumatin DNA inserted such that the single strand has the same polarity as the thaumatin mRNA; clone M13-101-B has the preprothaumatin DNA inserted such that the single strand has the opposite polarity as the thaumatin mRNA (FIG. 12).

8b. Production of DNA encoding prethaumatin

The single-stranded DNA of M13-101-A was used as a template for complementary DNA synthesis, using the chemically synthesized DNA sequence (5')pTCAGGCAGTAGGGC$_{OH}$(3') as a primer. After heat denaturation of the ds DNA, the complementary DNA strand served as a template for DNA synthesis using the fragment.

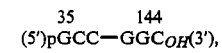

Figure 13:
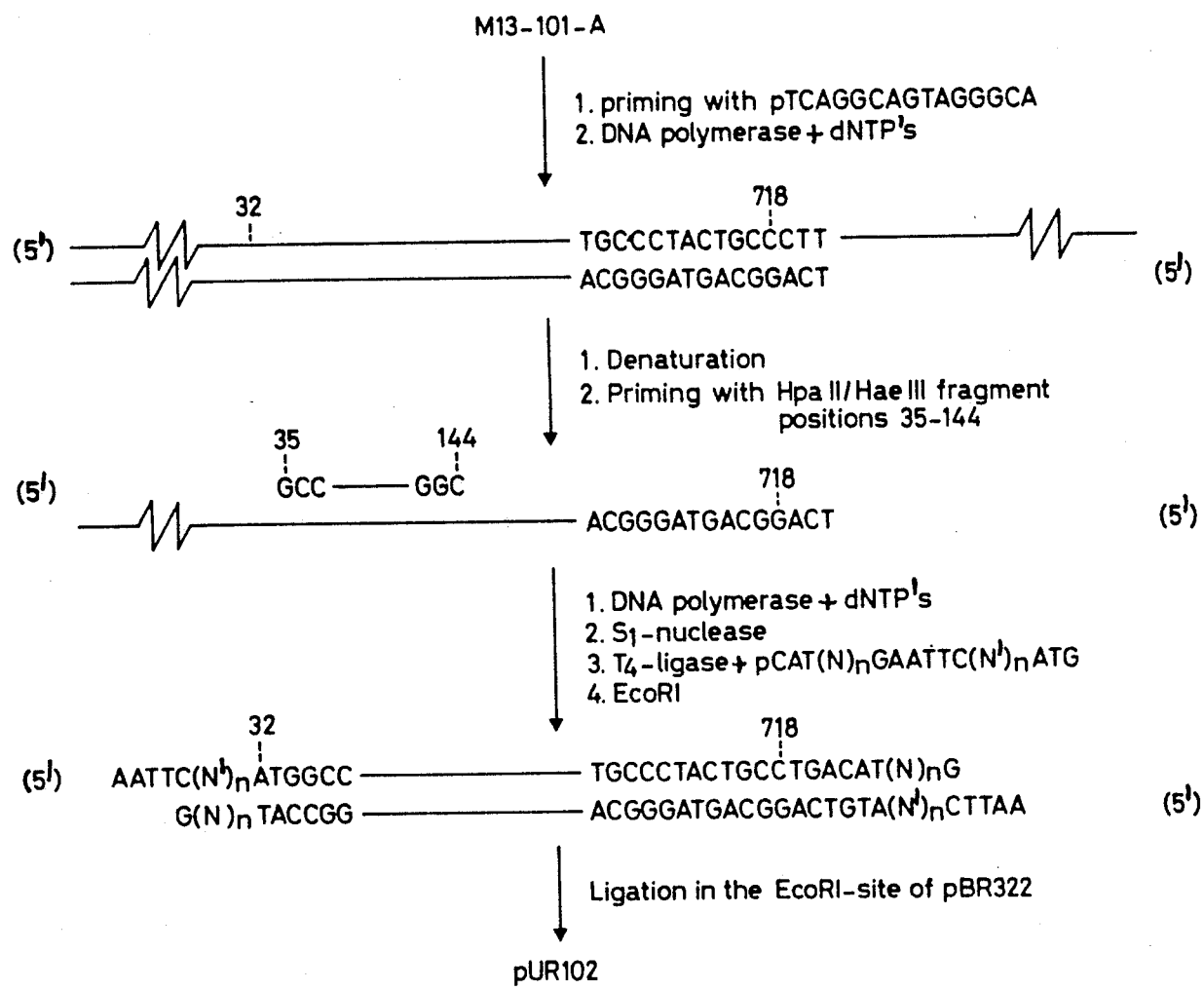

(5')pGCC—GGC$_{OH}$(3'), whose synthesis is described under 8a, as a primer. Subsequently, the obtained ds DNA fragment was treated with S1-nuclease and blunt end ligated with the EcoRI-linker (5')pCA GAATTC(N)$_n$GAATTC(N'-)$_n$ATG$_{OH}$(3') (FIG. 13). This DNA was digested with EcoRI and integrated in the EcoRI restriction site of pBR 322 resulting in plasmid pUR 102, containing the prethaumatin nucleotide sequence 32–718.

8c. Production of DNA encoding prothaumatin

Figure 14:
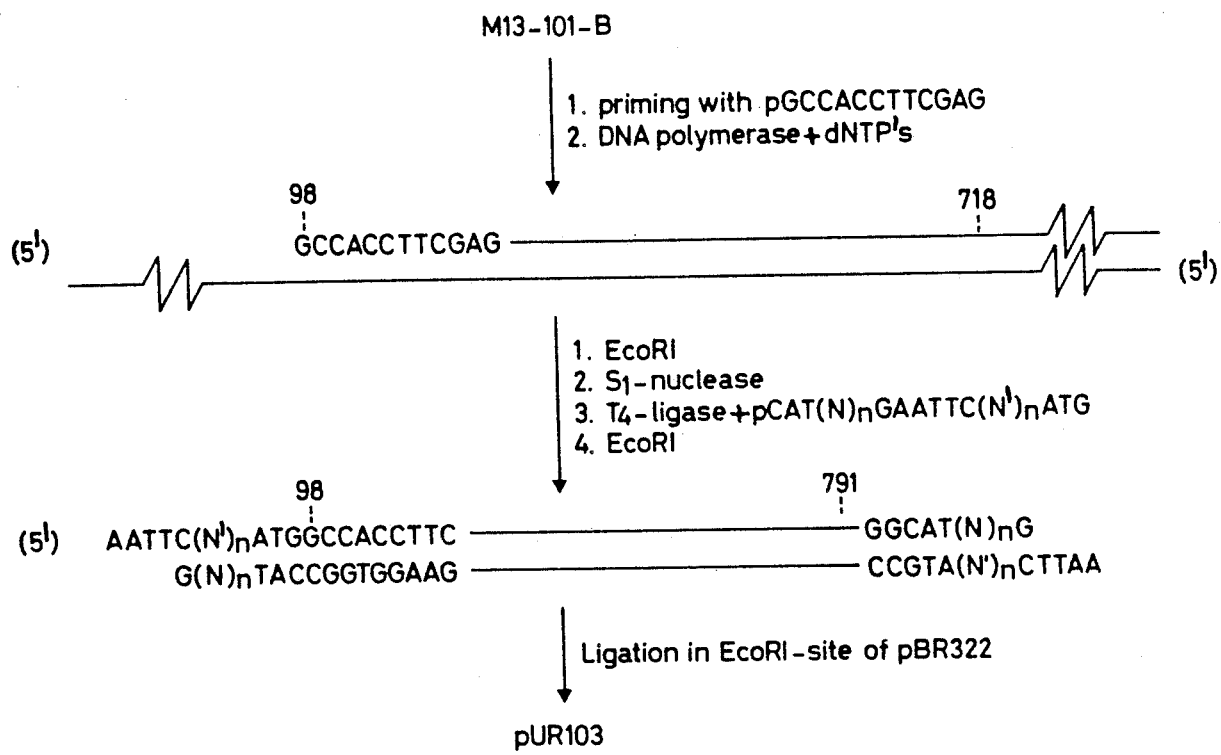

The single-stranded DNA of M13-101-B was used as a template for complementary DNA synthesis, using the chemically synthesized DNA sequence (5')pGCCACCTTCG$_{OH}$(3') as a primer. The formed ds DNA was treated with EcoRI and S1 nuclease and subsequently blunt end ligated with the chemically synthesized EcoRI linker (5')pCAT(N)$_n$GAATTC(N'-)$_n$ATG$_{OH}$(3'). This fragment was treated with EcoRI and then integrated in the EcoRI restriction site of pBR 322, resulting in the plasmid pUR 103, containing the prerothaumatin nucleotide sequence 98–736 (FIG. 14).

8d. Production of DNA encoding the unprocessed preprothaumatin, except that special mutations have been introduced into the nucleotide sequence 32–97, particularly into the nucleotides 32–49.

Figure 15:
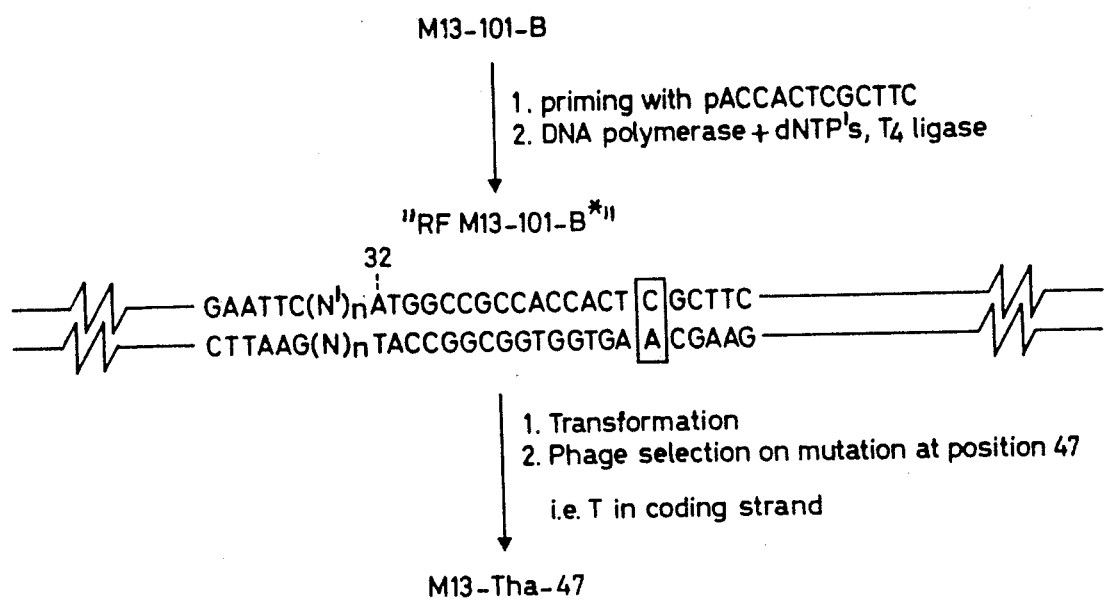
FIG. 15 shows the construction of M13-Tha47.

The single-stranded DNA of M13-101-B was used as a template for complementary DNA synthesis using the chemically synthesized DNA sequence (5')pAC-CACTCGCTTC$_{OH}$(3') as a primer. After transformation of E. coli with the ds DNA, the phage DNA with the mutation (T replaced by C at position 47) was selected by DNA sequence analysis. These phages were coded M13 Tha 47 (FIG. 15).

8e. Production of DNA coding for any of the sequences described under (8a–8d), except that special mutations have been introduced into the nucleotide sequence 32–736, particularly into the nucleotide sequence 332–718.

Figure 16:
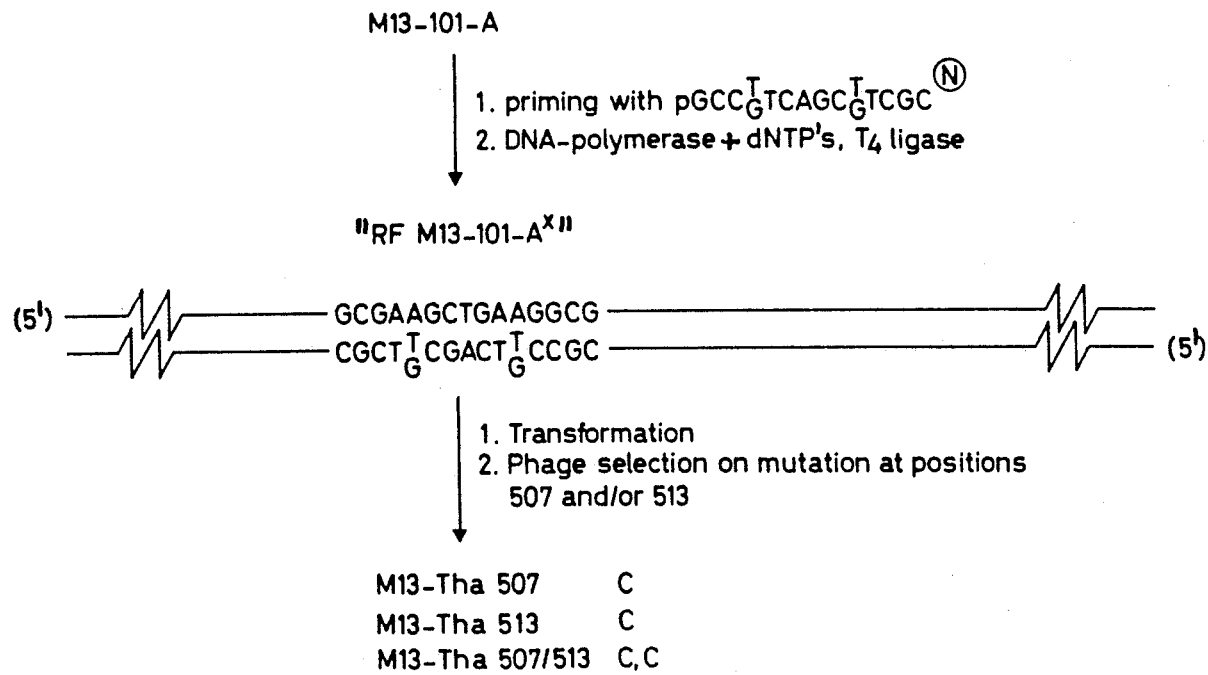
FIG. 16 shows the construction of M13-Tha507, M13-Tha513, and M13-Tha507/513.

The single-stranded DNA of M13-101-A was used as a template for DNA synthesis using the Klenow DNA-polymerase and the chemically synthesized primers (5')pGCCTTCAGCGTCGC$_{OH}$(3'), (5')pGCCGTCAGCTTCGC$_{OH}$(3') and (5')pGCCGTCAGCGTCGC$_{OH}$(3'). All these sequences are complementary to the nucleotides 503–516 of the preprothaumatin gene (FIG. 4) with one or two modifications to introduce the desired change in the protein. After transformation of E. coli with the ds DNAs, the phages with the modifications aimed at were selected by DNA sequence analysis. These phages were coded M13 Tha 507, 513, 507/513 (FIG. 16).

9a. Construction of a plasmid pUR 201

A fragment containing 285 base pairs comprising the double lac regulon (lac UV5) was obtained by restriction endonuclease EcoRI cleavage of pKB 268, (K. Backman and M.Ptashne, Cell 13, 65–71 (1978)). This fragment was ligated in the EcoRI site of pBR 322 DNA. Plasmid DNA with the lac regulon in the right orientation (FIG. 7) was partly cleaved by EcoRI in the presence of E. coli RNA polymerase. The EcoRI cleavage site most distant from the restriction endonuclease Hind III cleavage site was preferentially attacked. The linearized DNA was treated with S1 nuclease, purified by agarose gel electrophoresis, circularized by ligation with T4 DNA-ligase and subsequently used to transform E. coli. From the tetracycline-resistant transformants pUR 201 with the correct structure (FIG. 7) was obtained.

9b. Construction of plasmid pUR 301

A DNA fragment of about 510 base pairs was obtained by restriction endonuclease Hinf I cleavage of ptrp ED5 (R. A. Hallewell and S. Emtage, Gene 9, 27–47 (1980)). This fragment was cleaved with restriction endonuclease Taq I in the presence of E. coli RNA polymerase. The Taq I site in the trp regulon (described by K. Bertrand et al., Science 189, 22–26 (1975) and F. Lee et al., J. Mol. Biol. 121, 193–217 (1978)) was selectively protected, thus yielding a fragment containing 234 base pairs comprising the trp regulon (FIG. 8). This fragment was then treated with S1 nuclease, blunt-end ligated with the EcoRI-linker (5')pGGAATT-CC$_{OH}$(3'), cut with EcoRI and subsequently cloned in the EcoRI-site of pBR 322.

Plasmid pUR 300 with the trp regulon in the correct orientation (FIG. 8) was isolated. The EcoRI-cleavage site most distant from the Hind III site was removed by partial cleavage of pUR 300 DNA by EcoRI in the presence of ethidium bromide and S1 nuclease treatment. Linear DNA molecules were recircularized by T4 DNA ligase. From the tetracycline-resistant transformants pUR 301 with the structure as outlined in FIG. 8 was obtained.

9c. Construction of Plasmid pUR 401

A fragment containing 269 base pairs (DNA sequence 1128–1379) was obtained by digestion of RF M13 DNA (see P. M. G. F. V. Wezenbeek et al., Gene 11, 129–148 (1980)), with the restriction endonucleases Taq I and Hae III and the Taq I site was made blunt-ended by a repair reaction with E. coli DNA polymerase; the fragment was subsequently partly digested with restriction enzyme Mnl I. The partial products were treated with successive actions of T4 DNA polymerase and S1 nuclease and subsequently blunt-end ligated with the EcoRI-linker (5')pGGAATTCC$_{OH}$(3'), then treated with EcoRI and ligated in the EcoRI site of the pBR 322. By restriction enzyme analysis and DNA sequence analysis a plasmid was obtained in which the EcoRI cleavage site was located just beyond the ribosome-binding site of the M13 gene VIII DNA sequence. Applicants have found that the plasmids having the M13 regulon from nucleotide 1128 to nucleotide 1291 to 1297 were appropriate regulons for expression. The EcoRI cleavage site most distant from the Hind III site was removed essentially as described for pUR 301. The complete construction of pUR 401 is outlined in FIG. 9.

9d. Chemical synthesis of linkers and primers

The synthesis were carried out with the phosphotriester method described by J. F. M. de Rooy et al., Recl. Trav. Chim. Pays Bas, 98, 537–548 (1979).

10. Construction of expression plasmids comprising a constitutive or an inducible regulon and the ligated preprothaumatin genes described under (8a–8e) and transformation of E. coli with said plasmids.

Figure 17:
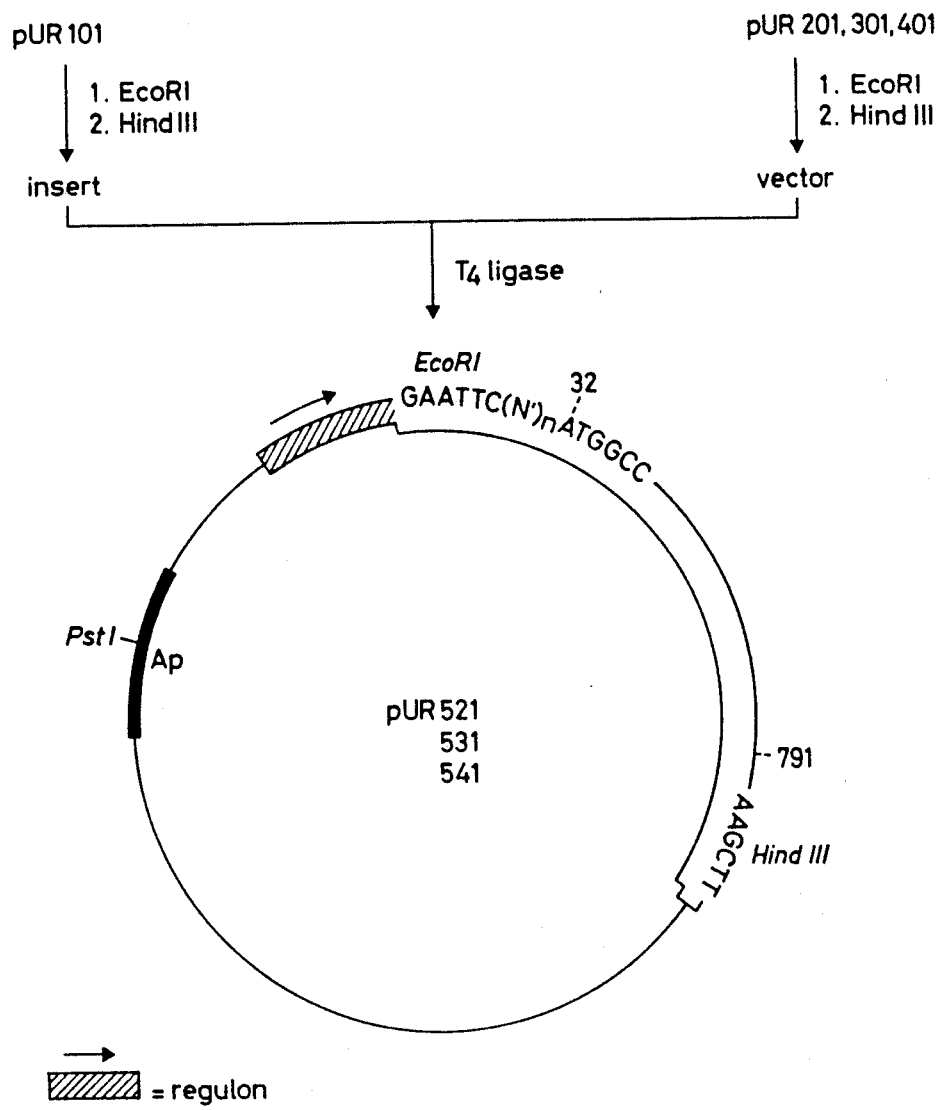
FIGS. 17–21 illustrate the construction of plasmids pUR 521–527, 531–537, an d541–547.

10a. The preprothaumatin encoding DNA fragment of plasmid pUR 101 was obtained by treatment of pUR 101 with the restriction endonucleases EcoRI and Hind III. Subsequently this DNA fragment was integrated in the EcoRI and Hind III site of the plasmids pUR 201 or pUR 301 or pUR 401, resulting in the expression plasmids pUR 521, pUR 531 and pUR 541 respectively (FIG. 17).

Figure 18:
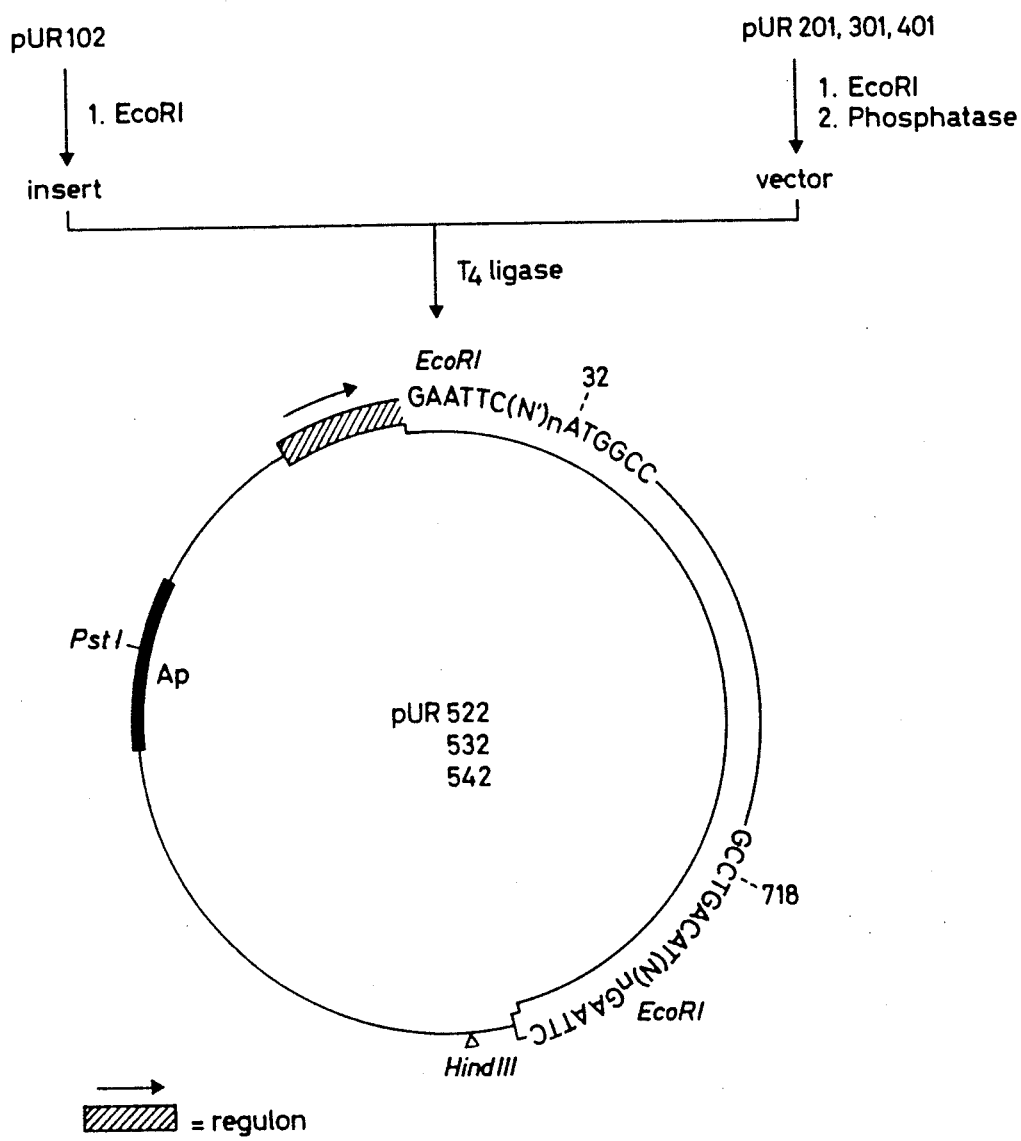

10b. The prethaumatin encoding DNA fragment of plasmid pUR 102 was obtained by treatment of pUR 102 with the restriction endonuclease EcoRI and subsequently integrated in the EcoRI site of the plasmids pUR 201 or pUR 301 or pUR 401 resulting in the expression plasmids pUR 522, pUR 532 and pUR 542 respectively (FIG. 18).

Figure 19:
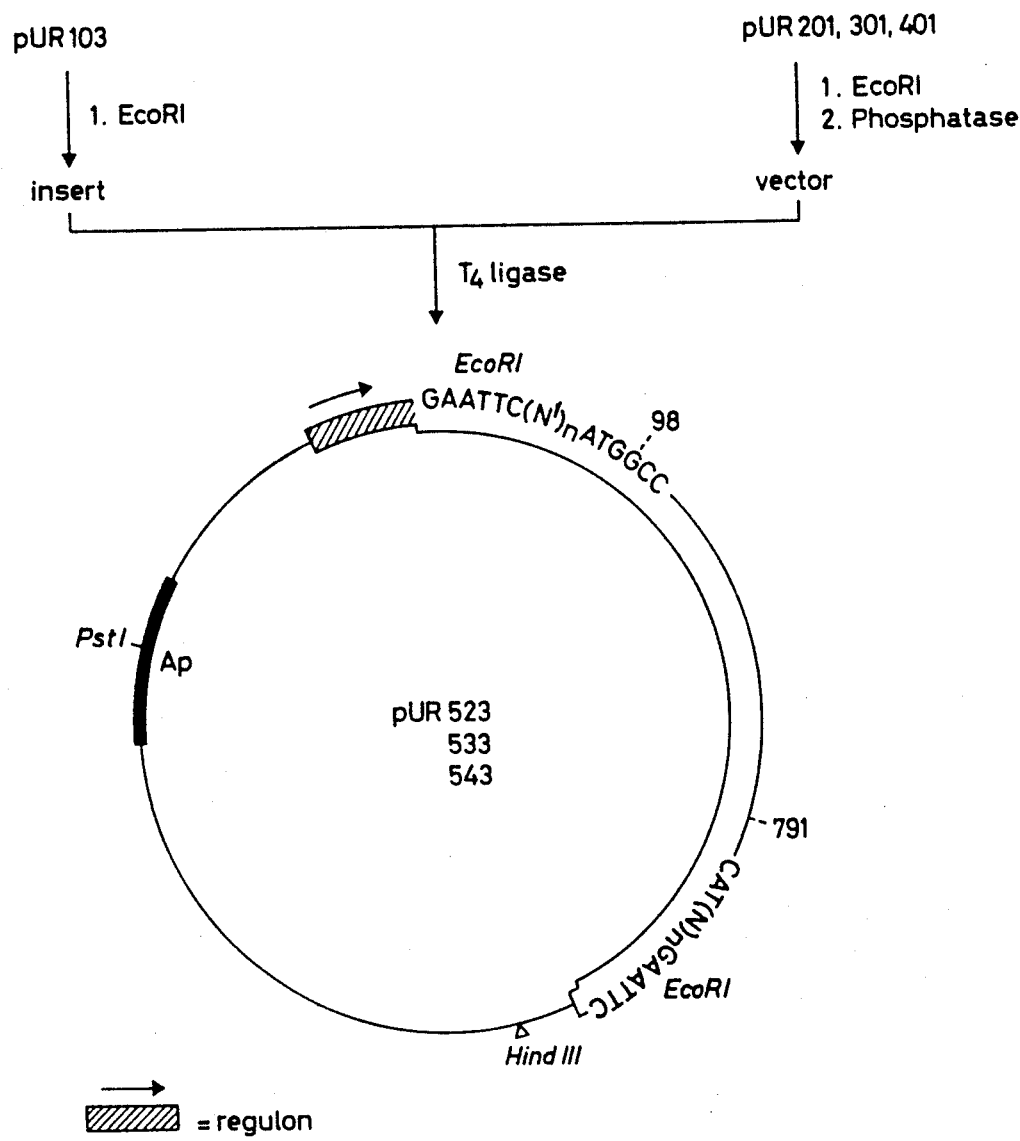

10c. The prothaumatin encoding DNA fragment of plasmid pUR 103 was obtained by treatment of pUR 103 with the restriction endonuclease EcoRI and subsequently integrated in the EcoRI site of plasmids pUR 201 or pUR 301 or pUR 401, resulting in the expression plasmids pUR 523, pUR 533 and pUR 543 (FIG. 19).

Figure 20:
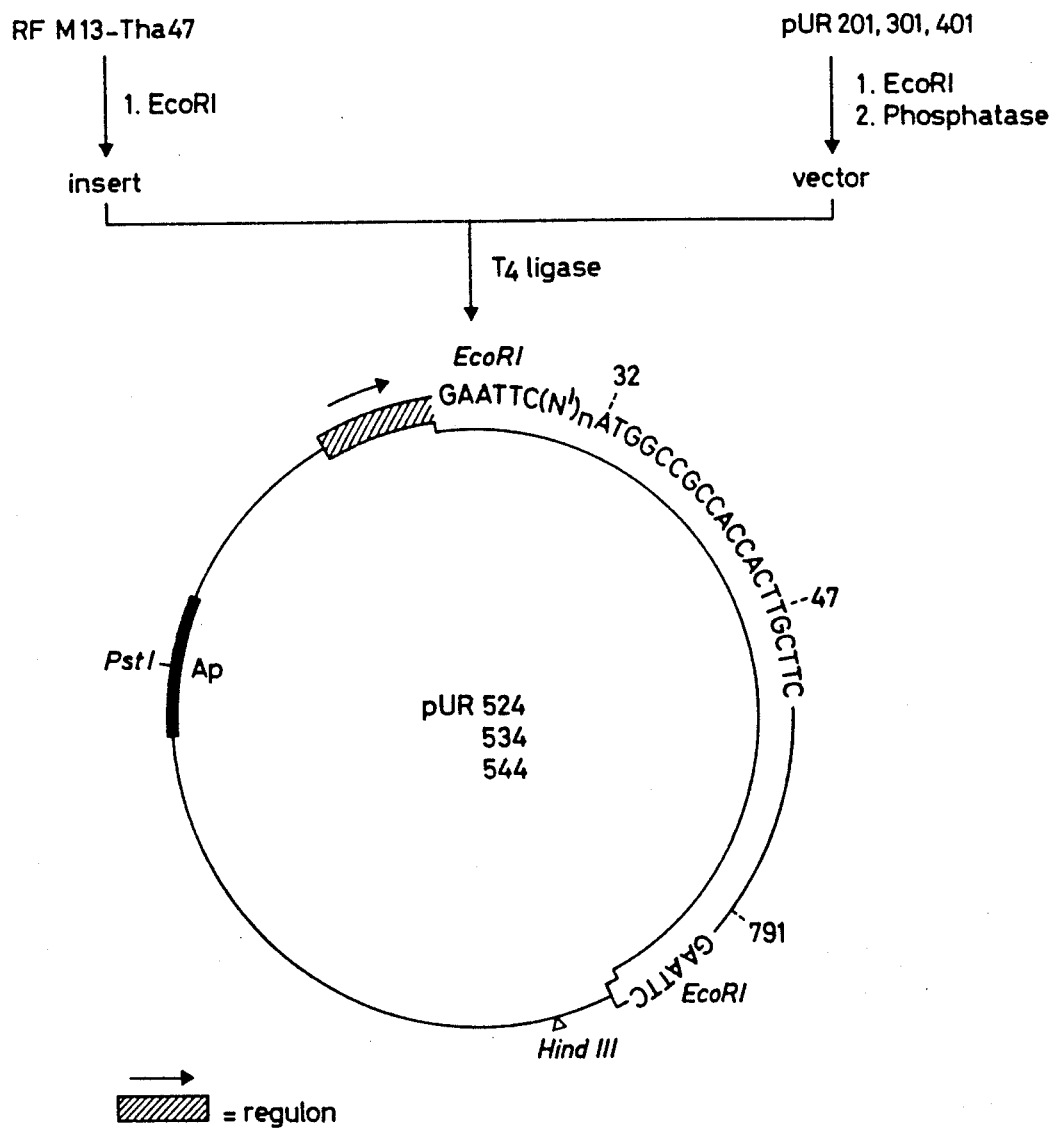

10d. RF M13 Tha 47 DNA was treated with EcoRI and the DNA fragment encoding preprothaumatin was subsequently integrated in the EcoRI site of plasmids pUR 201 or pUR 301 or pUR 401, resulting in the expression plasmids pUR 524, pUR 534 and pUR 544 respectively (FIG. 20).

Figure 21:
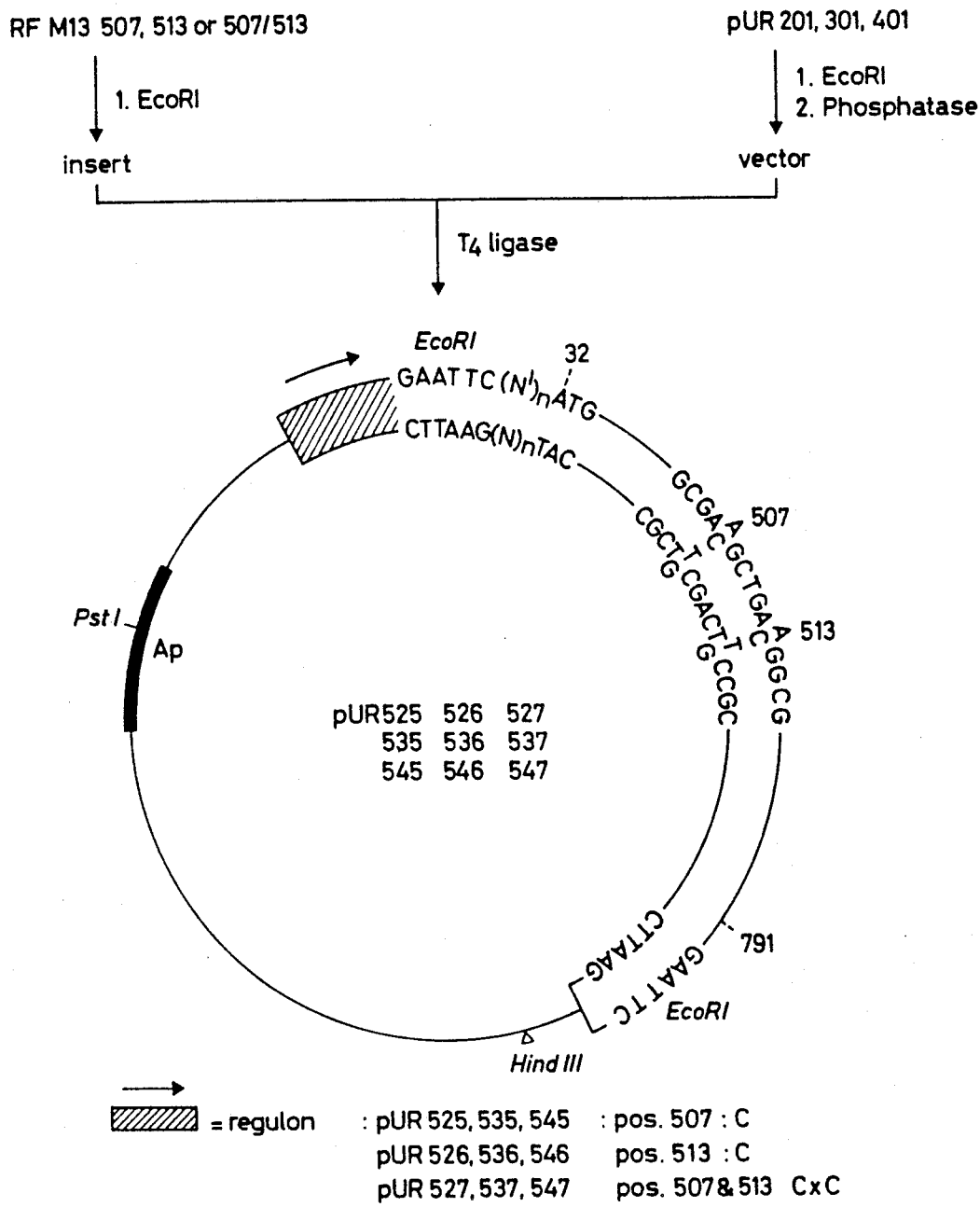

10e. RF M13 Tha 507 or RF M13 Tha 513 or RF M13 Tha 507/513 DNA was treated with EcoRI and the DNA fragments encoding the mutated forms of preprothaumatin were subsequently integrated in the EcoRI site of plasmids pUR 201 or pUR 301 or pUR 401, resulting in the double lac expression plasmids pUR 525-527 (containing preprothaumatin mutated at positions 507, 513 and 507 and 513 respectively), the trp expression plasmids pUR 535-537 (containing preprothaumatin mutated at positions 507, 513 and 507 and 513 respectively) and the M13 expression plasmids pUR 545-547 (containing preprothaumatin mutated at positions 507, 513 and 507 and 513 respectively) (FIG. 21). In all the plasmids described under (10a-10e) the AATT sequence originating from the chemically synthesized linkers could be deleted by cleavage of the plasmids with EcoRI in the presence of ethidium bromide; linear partials were isolated by agarose gel electrophoresis, treated with S1 nuclease and recircularized by T4 ligase. Plasmids with an AATT deletion were isolated by restriction enzyme analysis and the deletion was confirmed by DNA sequence analysis.

A culture of the following strains have been deposited in the permanent culture collection of the American Type Culture Collection, 12301 Parklawn Drive, Rockville, Md. 20852-1776, U.S.A.: *E. coli* strain K12 (294)-pUR522, ATCC 39016 (Dec. 2, 1981); *E. coli* strain K12 (294)-pUR523, ATCC 39017 (Dec. 2, 1981); and E. coli strain K12 (294)-pUR531, ATCC 39015 (Dec. 2, 1981).

11. Culturing of *E. coli* cells containing said plasmids and detection of preprothaumatin and its various maturation forms.

*E. coli* cells containing one of the plasmids pUR 521-527, pUR 531-537 and pUR 541-547 with or without the AATT sequence in the linker between the regulon and the preprothaumatin genes in the correct orientation and reading frame were cultured under optimal conditions for their growth - these culturing conditions vary with the type of plasmid present in the cells - but a suitable antibiotic was always present to maintain selection pressure.

Under these conditions the cells containing either plasmids pUR 521-527 or pUR 531-537 or pUR 541-547 produced considerable amounts of various forms of preprothaumatin.

The presence of the protein was demonstrated qualitatively by SDS gel electrophoresis of cell extracts from which preprothaumatin or its maturation forms were isolated by specific immunoprecipitation, by physiological tests on their sweetness and by a specially developed enzyme linked immunosorbent assay (Elisa). The antisera for this test were generated by injecting the thaumatin produced by the plant *Thaumatococcus daniellii* supplemented with Freund adjuvant in sheep as well as in rabbits.

We claim:

1. A DNA fragment consisting essentially of a structural gene encoding a protein selected from the group consisting of preprothaumatin, prethaumatin and prothaumatin.

2. A process of producing preprothaumatin, prethaumatin, proothaumatin or thaumatin, which process comprises:
   (i) transforming a host cell with a recombinant DNA molecule comprising a cloning vehicle capable of transforming said host cell, and a structural gene encoding a protein selected from the group consisting of preprothaumatin, prethaumatin and prothaumatin;
   (ii) culturing said transformed host cell under conditions such that said protein is produced; and
   (iii) isolating said protein.

3. A recombinant DNA molecule comprising a cloning vehicle capable of transforming a host cell, and a structural gene encoding a protein selected from the group consisting of preprothaumatin, prethaumatin and prothaumatin.

4. The recombinant DNA molecule according to claim 3 wherein said host cell is a microbial host cell.

5. A transformed host cell comprising said recombinant DNA molecule as claimed in claim 3.

6. The transformed host cell according to claim 5, wherein said host cell is a microbial host cell.

* * * * *

UNITED STATES PATENT AND TRADEMARK OFFICE
CERTIFICATE OF CORRECTION

PATENT NO. : 4,966,842

DATED : October 30, 1990

INVENTOR(S) : Verrips et al

It is certified that error appears in the above-identified patent and that said Letters Patent is hereby corrected as shown below:

Column 10, Claim 2, line 2, correct the spelling of "prothaumatin".

Signed and Sealed this

Eighth Day of September, 1992

Attest:

DOUGLAS B. COMER

*Attesting Officer*  *Acting Commissioner of Patents and Trademarks*